(12) United States Patent
Holvoet et al.

(10) Patent No.: US 8,911,803 B2
(45) Date of Patent: Dec. 16, 2014

(54) NUTRITIONAL COMPOSITION COMPRISING AN APPLE EXTRACT AND REDUCING FOOD ALLERGY SYMPTOMS, ESPECIALLY IN CHILDREN

(75) Inventors: Sebastien Holvoet, Savigny (CH); Annick Mercenier, Bussigny (CH); Adrian Zuercher, Bern (CH)

(73) Assignee: Nestec S.A., Vevey (CH)

( * ) Notice: Subject to any disclaimer, the term of this patent is extended or adjusted under 35 U.S.C. 154(b) by 243 days.

(21) Appl. No.: 13/260,814

(22) PCT Filed: Apr. 23, 2010

(86) PCT No.: PCT/EP2010/055431
§ 371 (c)(1),
(2), (4) Date: Sep. 28, 2011

(87) PCT Pub. No.: WO2010/124997
PCT Pub. Date: Nov. 4, 2010

(65) Prior Publication Data
US 2012/0021078 A1    Jan. 26, 2012

(30) Foreign Application Priority Data
Apr. 28, 2009  (EP) .................................. 09158980

(51) Int. Cl.
*A61K 36/73*    (2006.01)
*A23L 1/29*    (2006.01)
*A23L 1/30*    (2006.01)
*A23L 1/305*    (2006.01)

(52) U.S. Cl.
CPC ........... *A23L 1/3002* (2013.01); *A23V 2002/00* (2013.01); *A23L 1/296* (2013.01); *A23L 1/3053* (2013.01)
USPC ......................................... 424/765; 424/439

(58) Field of Classification Search
None
See application file for complete search history.

(56) References Cited

FOREIGN PATENT DOCUMENTS

| EP | 2044851 | 4/2009 |
|----|---------|--------|
| JP | 2006096694 | 4/2006 |
| JP | 2009060800 | 3/2009 |
| WO | WO 2006003750 | 1/2006 |

OTHER PUBLICATIONS

English translation of Yamada (JP 2009-060800) Mar. 2009.*
English translation of Toshihiko (JP 2006-096694) 2006.*
Paquatte (Household and Personal Care Today (Feb. 2007), pp. 16-17).*
Akiyama et al., "Dietary unripe apple polyphenol inhibits the development of food allergies in murine models" FEBS Letters, Elsevier, vol. 579, No. 20, Aug. 15, 2005, pp. 4485-4491, XP005010831.
Takano et al., "Aqueous extract of peanut skin and its main constituent procyanidin AI suppress serum IgE and IgG1 levels in mice-immunized with ovalbumin," Biological & Pharmaceutical Bulletin, vol. 30, No. 5, May 2007, pp. 922-927, XP002536854.
Takatsugu et al., "Anti-allergic effect of apple ployphenol on patients with atopic dermatitis: A pilot study," Allergology International, vol. 49, 2000, pp. 69-73.
Kishi, et al., "Clinical Efficacy of Apply Polyphenol for Treating Cedar Pollinosis," Biosci. Biotechnol. Biochem., vol. 69 No. 4, 205, pp. 829-832, 2005.
Kimata et al., "Effects of luteolin, quercetin and baicalein on immunoglobulin E-mediated mediator release from human cultured mast cells," Clinical and Experimental Allergy: Journal of the British Society for Allergy and Clinical Immunology, 2000, vol. 30, No. 4, pp. 501-508.
Dorsch et al., "Antiasthmatic Effects of *Galphimia glauca*, Gallic Acid, and Related Compounds Prevent Allergen- and Platelet-Activating Factor-Induced Bronchial Obstruction as well as Bronchial Hyperreactivity in Guinea Pigs," Int. Arch Allergy Immunol., 1992, vol. 97, pp. 1-7.
Nair et al., "The flavonoid, quercetin, differentially regulates Th-1 (IFNy) and Th-2 (IL4) cytokine gene expression by normal peripheral blood mononuclear cells," Biochem, Biophys. Acta., vol. 1593, 2002, pp. 29-36.
Search Report for International Application No. PCT/EP2010/055431 mailed Jun. 30, 2010.
Written Opinion of International Application No. PCT/EP2010/055431 mailed Jun. 30, 2010.
Q. Dingkun, et al. (College of Light Industry and Foods, South China University of Technology), "Recent Advances in Food Desensitization Technology," Food and Fermentation Industries, Jul. 2006, 5 pages.
Tang Chuanhe, et al.,(Food and Biological Institute of Southern China, University), Guangzhou 510640, "The Development and Application of Apple Polyphenol," [J], China Food Additives, Feb. 2001-2002, 6 pages.

* cited by examiner

*Primary Examiner* — Susan Hoffman
(74) *Attorney, Agent, or Firm* — K&L Gates LLP (57) ABSTRACT

A complete nutritional composition comprising polyphenols is provided for reducing the symptoms of allergies originating from food allergens in young children or infants. Preferably the composition modulates the secondary prevention of allergies while not affecting significantly the primary prevention. The composition comprises an apple extract.

15 Claims, 6 Drawing Sheets

Figure 5 (Table 1) Gene expression levels in ileal Peyer's patches

| Target gene | Relative gene expression (median±SEM and fold change) | | | | | |
|---|---|---|---|---|---|---|
| | Neg Control | | Pos Control | | Apple Extract Pomactiv HFV | |
| | Relative[1] | Fold[2] | Relative | Fold | Relative | Fold |
| IL-5 | 1±4 | 1 | 45±19 | 85.3 | 1±21 | 2.5 |
| IL-13 | 1±4 | 1 | 175±50 | 324.0 | 48±49 | 88.9 |
| CCL11 | 491±308 | 1 | 2388±1078 | 4.9 | 974±1981 | 2.0 |
| CCL17 | 245±42 | 1 | 1994±687 | 8.1 | 1288±366 | 5.3 |
| GATA3 | 3103±300 | 1 | 3622±462 | 1.2 | 4549±615 | 1.5 |
| IL-10 | 197±34 | 1 | 913±108 | 4.6 | 445±95 | 2.3 |
| IL-12a | 1372±145 | 1 | 2163±605 | 1.6 | 1974±327 | 1.4 |
| IFN-γ | 74±28 | 1 | 220±102 | 3.0 | 83±20 | 1.1 |

[1]Relative gene expression levels were normalized to 3 house keeping genes (GAPDH, β-actin, HPRT)
[2]Fold expression was normalized to expression levels in the Neg Control group Figure 6 (Table 2). Gene expression levels in ileum

| Target gene | Relative gene expression (median±SEM and fold change) | | | | | |
|---|---|---|---|---|---|---|
| | Neg Control | | Pos Control | | Apple Extract Pomactiv HFV | |
| | Relative | Fold | Relative | Fold | Relative | Fold |
| IL-5 | 8±47 | 1 | 15±403 | 1.8 | 16±114 | 1.9 |
| IL-13 | 6±1 | 1 | 648±360 | 100.5 | 277±105 | 43.0 |
| CCL11 | 4703±3286 | 1 | 18038±6797 | 3.8 | 2118±1352 | 0.5 |
| CCL17 | 359±177 | 1 | 3754±888 | 10.5 | 2203±543 | 6.1 |
| GATA3 | 2920±845 | 1 | 5827±1191 | 2.0 | 2302±1059 | 0.8 |
| IL-10 | 306±163 | 1 | 2604±1540 | 8.5 | 615±602 | 2.0 |
| IL-12a | 100±148 | 1 | 830±438 | 8.3 | 190±323 | 1.9 |
| IFN-γ | 775±308 | 1 | 1747±738 | 2.3 | 631±196 | 0.8 |

[1]Relative gene expression levels were normalized to 3 house keeping genes (GAPDH, β-actin, HPRT)
[2]Fold expression was normalized to expression levels in the Neg Control group

NUTRITIONAL COMPOSITION COMPRISING AN APPLE EXTRACT AND REDUCING FOOD ALLERGY SYMPTOMS, ESPECIALLY IN CHILDREN

CROSS REFERENCE TO RELATED APPLICATIONS

The present application is a National Stage of International Application No. PCT/EP2010/055431, filed on Apr. 23, 2010, which claims priority to European Patent Application No. 09158980.4, filed on Apr. 28, 2009, the entire contents of which are being incorporated herein by reference.

FIELD OF THE INVENTION

This invention relates to the use of a natural extract comprising polyphenols in the manufacture of a nutritional composition for reducing the allergic symptoms of allergic patients when exposed to allergens.

BACKGROUND TO THE INVENTION

Allergies are among the most common health problem affecting the life of patients of all age. Allergic diseases are nowadays recognized as an epidemic by the WHO. The prevalence of allergies has been shown to increase in the past decades. Modern life style, especially urban, has been associated with high prevalence and higher severity of allergic manifestations.

Allergic sensitization in childhood, especially in early childhood and especially to food allergens, is critical and of highest interest as development of an "allergic phenotype" or "atopy" has been shown to facilitate subsequent sensitization to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblöm et al 2008). Children with milder forms of food hypersensitivity also have increased risk for development of respiratory allergies but to a lesser degree than children with persistent food hypersensitivity. Therefore, attenuating the severity of food hypersensitivity may be crucial for slowing down the "Atopic March".

In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Prevention of allergies can be achieved on different levels:

"Primary prevention" is the effect of preventing or reducing the risk of sensitization of patients to allergens, characterized by absence or reduced levels of allergen-specific IgE antibodies. Preventing or reducing sensitization will result in absence or reduction of allergic symptoms upon exposure to the same allergen. By modulating the way a patient gets sensitized in regard to one allergen or one group of allergens (primary prevention), the subsequent allergic response may also be modulated.

"Secondary prevention" is the effect of modulating the symptoms of allergies, i.e. the occurrence or intensity of the allergic reaction in patient already sensitized to one or several allergens when the patient is re-exposed to said allergen(s). By modulating the occurrence or intensity of the allergic symptoms (secondary prevention), the inconvenience associated with allergies is minimized.

Given these distinct concepts of allergy prevention it may be hypothesized that by virtue of their inherent mechanisms of action, some compounds might act solely at one or at both of these specific levels of prevention. Some may, for example, solely reduce the sensitization to a specific allergen (primary prevention), while other compounds may solely have merely an effect on the secondary prevention and reduce the severity of allergic reactions. Other compounds may be able to influence both sensitization and symptoms and thus are effective in promoting primary and secondary prevention.

Food allergens are among the first allergens that infants encounter in their early life: typically, cow's milk proteins may be encountered by infants not receiving exclusive breast-feeding. Milk-proteins are indeed among the most frequently observed cause for food allergy in infancy, followed by eggs and wheat proteins. In general, food allergies can manifest by cutaneous (rash, eczema, others) and gastrointestinal symptoms (abdominal cramps, pain, especially in the abdomen, vomiting) in infants and young children. Further sensitization and episodes of allergies can also appear when the infant/young child is exposed to a novel food such as cereals, vegetables or fruits.

Polyphenols are a large group of small compounds with anti-oxidant activity that are commonly found in plants and fruits. Flavonoids are a subgroup of polyphenols with shared structural features that themselves can be further sub-grouped (again based on common structures) for examples into flavonols, flavanols, flavones, flavanones and others. Compounds contained in apples have been used and, demonstrated to have a general effect on allergies: flavonoids such as quercetin as well as other polyphenols have been suspected to provide a beneficial effect on allergies in general. Apples are rich in various polyphenols, including quercetin and phlorizidin. In vitro and in vivo experiments in laboratory animals suggested that some polyphenols might be able to reduce allergic reactions via a mechanism similar to common anti-histaminics (i.e. inhibitory effect on mast-cell degranulation). This has been described in particular in M. Kimata et al., Clin. Exp. Allergy 2000; 30: 501-508; M. P. Nair et al., Biochim. Biophys. Acta 2002; 1593: 29-36 and W. Dorsch et al., Int. Arch. Allergy. Immunol. 1992; 97: 1-7. Furthermore Kojima et al describe in Allergology International (2000) 49:69-73 that apple polyphenols can have a beneficial effect on atopic dermatitis. In Biosci. Biotechno, Biochem. 69 69(4), 829-832, 2005, Kishi et al. describe the efficacy of apple polyphenol for treating cedar pollinosis.

However there remains a need for specifically reducing allergic reaction and symptoms especially in the population of young children and infants.

The question of food born allergic reaction in the young age is even further complicated by the specific nutritional needs of infants and young children.

Caloric intake, caloric density, variety of desirable nutrient, protein content and protein quality are all among the factors important to bring the most appropriate nutrition to infants and young children. The presence of micronutrients such as vitamins and minerals are also of importance, more specifically when their presence is limited by specific defined ranges corresponding to the age of the target patients. As such, for the young children and infants, the matrices of food delivery are inherently complex but they are also of less variety: for example infants, although potentially allergic, require a specific protein balance in a matrix of milk-derived proteins. The presence of such multiple nutrients can potentiate the effect of the food allergens. In such complex matrices, low key food allergens unable to trigger allergic manifestation alone, can then become more powerful at initiating an allergic reaction. Similarly compounds that may neutralize allergens or act on allergy prevention may see their effect diminished or annihilated in such complex nutritional matrices. Specifically it is not predictable whether compounds usually recognized to act on allergy prevention would still be active, and to which extend, in complex matrices such as nutritional composition for infants or young children.

There is a need to bring relief in the symptoms of food allergies in populations of infants and young children that have a history of allergic episodes and/or are allergic.

There is a need to provide a complete nutritional composition that not only brings a variety of nutrients but also reduces the severity of allergic reactions.

There is a need for providing a nutritional composition modulating the allergic reaction of young patients suffering from light to moderate forms of allergies, as these patients have special needs dictated by the low maturity of their intestinal and immune systems.

There is also a need for modulating allergic reactions in young children that do not tolerate stringent pharmaceutical molecules, for example by nutritional interventions such as including modulators of the immune system into the regular nutritional regimen.

There is a need for providing a nutritional composition modulating the allergic reaction of young patients at the time, and around the time of weaning when the intestinal tract undergoes severe modification and when new potentially allergenic solid foods are introduced and hence the patient is particularly susceptible to the sensitization to food allergens.

There is a need for alleviating the symptoms of allergies by providing an effective composition, possibly by reducing the exposure to allergens, even though the composition may not directly reduce the sensitization to allergens.

There is a need for a composition that has a positive effect on secondary prevention of allergy while not necessarily acting on the primary prevention to the same allergies.

There is finally a need for a composition, most particularly suited for young patients that by reduction of symptoms can help to diminish the "allergic phenotype" and thus can lower sensitization later in life to new allergens. There is a need for attenuating the atopic march.

SUMMARY OF THE INVENTION

In a first aspect, the present invention provides a complete nutritional composition for reducing the symptoms of allergies originating from food in patients having allergies triggered by food allergens, especially in infants and/or young children.

In a second aspect, the present invention provides a composition that significantly promotes secondary prevention of allergic reactions triggered by food allergens, optionally while not affecting the primary prevention against the same allergens.

In a third aspect, the present invention provides a composition that is enriched in polyphenols, especially in quercetin.

In another aspect of the invention the composition of the invention is especially effective for infants and/or young children at the time of weaning.

The invention further extends to reduction of the sensitization to other allergens later in life.

DETAILED DESCRIPTION OF THE INVENTION

Definitions: In this specification, the following terms have the following meanings:

"Complete nutritional composition". For the purpose of this document a complete nutritional composition is a composition that comprises a significant amount, usually 50% or more, of the major nutritional nutrients recommended for a given age. Such major nutrients are usually provided in quantity and proportion such as to fulfil 50% or more of the specific recommended nutrient's doses for a given age, when used in adequate quantity for providing the recommended caloric intake for a given age. A complete nutritional composition usually comprises a source of protein, a source of lipid, a source of carbohydrates in a balanced proportion that meets the general recommendation for a given age. It usually also include micronutrients such as vitamins and minerals, as well as a source of essential amino acids and a source of essential fatty acids. It is however understood that a complete nutritional composition may not comprise all specific nutrients, nor all recommended amounts, to fulfil all nutritional needs of an infant or young child. A complete nutritional composition excludes compositions comprising merely apple extracts or apple extracts in a predominant proportion.

"Symptoms of allergies" generally include symptoms triggered by allergens. Such symptoms include cutaneous (redness of skin, rash, itchiness, dermatitis, eczema), ocular (itching and watering of the eyes), gastrointestinal (congestion, abdominal pain, cramps, vomiting diarrhea), respiratory (itching of the nose, nasal congestion, rhinitis, asthma) and in severe cases systemic (dizziness, mental confusion, anaphylaxis) manifestations.

"Primary prevention of allergies" means all measures aiming at avoidance or reduction of allergic (immunological) sensitization for example prevention or reduction of specific IgE antibodies.

"Secondary prevention of allergies" means prevention of the development of allergic disease/allergic symptoms in a sensitized individual.

"Weaning period" is the period during which infants are adapting from pure liquid nutrition to solid or semi-solid food, and adapting from quasi unique food type (generally mother milk or infant formula) to a variety of foods.

"Sensitization" means induction/development of allergen-specific IgE antibodies.

"Children/Young children/infants/Babies": Since children or infants are in particular affected by food allergies, the composition of the present invention is intended for, but not limited to, children and/or infants. According to the definitions appearing in Article 2 of the European Commission Directive 2006/141/EC of 22 Dec. 2006 on infant formulae and follow-on formulae "Infants" are children under the age of 12 months and young children are children between 1 and 3 years of age. The term "children" comprises the age groups from 1 to 14 years. Babies may be equivalent to infants and/or young children.

The inventors have evidenced that allergic reaction and symptoms can be alleviated when sensitized young mammals are provided with a complete nutritional composition that comprises an apple extract. This defined a positive effect on the secondary prevention of allergies.

Surprisingly this effect was not accompanied by a reduction of the sensitization of the young mammals to allergens (i.e. no primary prevention of allergies was evidenced).

Effect of the Composition:

The invention relates to the use of an apple extract comprising polyphenols for the manufacture of a complete nutritional composition for reducing the symptoms (of allergies originating from food) in patients having allergies triggered by food allergens. The inventors have evidenced that the apple extract is capable to reduce the symptoms of food allergy in a group of mice receiving a nutritional composition containing apple extract. This is evidenced when an allergic reaction (challenge) is induced after sensitization. The model mimics food allergy in humans, when humans (typically infants/young children) are naturally sensitized to food allergens. The apple extract hence shows a protective effect. Without being bound by the theory it is believed that polyphenols of the apple extract interact with the complete nutritional composition (in particular the fatty or proteinic components) to deliver an enhanced effect.

In one embodiment of the invention the effect of the composition is more specifically an effect on the secondary prevention of allergies. The symptoms of allergies, in the mouse model, are indeed reduced significantly, as illustrated by a lower allergic clinical score. Generally the symptoms can include all or a selection of the usually recognized symptoms of allergies.

In one embodiment of the invention the symptoms comprise diarrhea, skin irritation or respiratory symptoms or combination thereof.

In one embodiment of the invention the symptoms are accompanied by release of biochemical mediators, such a tryptase, chymase, histamine, leukotriens.

In one embodiment of the invention the composition however has no effect on the sensitization of the patients to the allergens. Indeed primary prevention seems not to be achieved by the composition comprising apple extract. The patients are still sensitized to the food allergens, but develop less symptoms of allergy when re-exposed to the sensitizing allergen. Without being bound to the theory it is believed that the effect therefore does not reduce the natural immune defences (which have a positive effect for the patient) but simply reduces the expression of the symptoms of allergy.

In one embodiment the composition reduces the sensitization to other allergens later in life. It is believed that the composition promotes (or at least does not block) the natural processes of immune maturation and hence, is able to have a long term effect on lowering the sensitization to the same allergens or to different allergens (reduction of sensitization later in life). By solely reducing the symptoms of allergy (secondary prevention), it is hypothesized that the composition of the invention can allow for the natural immune maturation to occur, and have such long term beneficial effect.

Composition of the Invention:

In one embodiment of the invention the composition comprises an apple extract that is rich in polyphenols. The apple extract is indeed enriched in polyphenols in comparison to a crude apple extract (without enrichment). In one embodiment the enrichment factor is at least 1.5, at least 2 or at least 5. It appears critical to the effect of the composition that the apple extract is sufficiently concentrated (enriched in polyphenols) to permit development and exertion of the anti-allergic effect. The effect could be mediated by blocking the release of allergic mediators from effector cells such as mast-cells (an effect comparable to anti-histaminic drugs). Without being bound by the theory, it is also believed that some of the compounds present in significant amount in the apple extract can bind the proteinic allergens and mask them form being recognized by the host immune system. It can not be excluded that the apple extract (possibly the active polyphenols) react with the specific proteins of the composition (proteins present in the composition—especially the milk-derived proteins) to form complexes and to mask the potential allergens.

In one embodiment of the invention, the composition comprises between 0.01% w/w and 3% w/w of apple extract. In one embodiment the composition comprises between 0.1% (w/w) and 1% (w/w) of apple extract or between 0.4% (w/w) and 0.6% (w/w). While it is crucial that a sufficient amount of apple extract is present to induce the desired effect, a quantity of apple extract that would be too high would have a negative effect by negatively impacting the composition (un-balance of nutrients). This means, complexing too much protein could alter the composition's content of bioavailable protein.

In one embodiment of the invention the apple extract is the protein extract commercialized by Val de Vire Bioactives (Conde sur Vire, France) under the reference "Pomactiv HFV". In one embodiment the apple extract is similar to or derived from the cited Pomactiv HFV and has similar effect.

In one embodiment of the invention the composition comprises quercetin. Quercetin may be comprised in the apple extract, in particular in the polyphenolic components of the apple extract. Specifically quercetin can bind/complex proteins of the complete nutritional composition including allergenic proteins contained in the composition and the complexing can contribute to the anti-allergic effect by sequestering the allergens from the immune system.

In one embodiment of the invention the composition comprises hydrolyzed or partially hydrolyzed proteins. A nutritional composition based on (partially) hydrolyzed proteins is particularly suited to the immune system and gastro-intestinal tract of infants/young children because hydrolyzed proteins are more easily digested and have reduced allergenicity compared to intact proteins. Furthermore it can be hypothesized that hydrolyzed proteins can be very efficiently bound by the polyphenols of the apple extracts—for example because of their relative size. This may trigger an enhanced masking effect of the allergens and thus may further reduce the allergenicity of the composition. This represents a most appropriate composition for the immune system and gastro-intestinal tract of a food-allergic infant/young child. In such instance the combination of the apple extract with hydrolyzed proteins is of highest relevance to the invention.

In one embodiment the hydrolyzed proteins are proteins hydrolyzed from whey proteins and/or casein. In one embodiment the hydrolyzed proteins results from the action of trypsin and/or chymotrypsin on the proteins (esp. whey proteins). In one embodiment the hydrolyzed proteins comprise soy proteins or/and egg proteins. In one embodiment the hydrolyzed proteins results from the action of proteases such as Protamex® and/or Flavourzyme® (Novozyme, Denmark). In one embodiment the proteins of the composition, preferably the hydrolyzed proteins, comprise cereal or eggs proteins. In one embodiment the hydrolyzed proteins results from the action of Alcalase. The composition of the invention can comprise a mix of 2 or more of the cited protein sources.

Target Group:

The composition of the invention is most suitably targeted at relatively young patients, although an effect on adults can not be excluded. Preferentially indeed the patients are sufficiently young to still going through a maturation phase of their immune system and their gastro-intestinal tract. In such patients the effect of the composition can be more intense or more rapid. In one embodiment the composition is an infant formula, an follow up formula, a growing-up milk, an infant cereal and/or a baby food. Follow-up formula are usually understood as compositions for infants after the 6 first months of life. Growing-up milk are usually understood as compositions for toddlers and/or children between 1 or 2 and 6 years of age or between 2 or 3 and 5 years. Growing-up milk are usually cow milk-based compositions. Preferably the composition is targeted at infants or young children or young humans below the age of 6, between birth and the age of 3, or between birth and weaning. In one embodiment the composition is a starter or a follow-up infant formula. Preferably the nutritional composition comprises a vast majority of the necessary nutrients for the feeding of the young humans.

In one embodiment the nutritional composition is an infant cereal composition for infants/young children 1 to 4 years old. The composition can be more specifically targeted to and administered during the weaning period and/or up to 12 months thereafter. The weaning period is indeed important in regard to the invention as the infants are exposed to a variety of foods during the weaning period, while undergoing a rapid maturation of their immune system and their gastro-intestinal tract. Effective control of the allergic response is therefore of particular importance during that period.

In one embodiment the nutritional composition of the invention is a growing-up milk targeted to and specifically formulated for toddlers between 1 and 3 or children between 3 and 6 years of age. The composition is based an cow milk and may contain probiotics and/or prebiotics. The composition can be part of a continuing regimen between 1 and 6 and be administered both during period of 1 to 3 and then between 3 and 6 years of age. Such administration may not be daily but may be sufficiently regular (e.g. at least once every month or week) to induce the intended effect. By acting at the key period(s) of immune system maturation and by being administered over a long period of time, the effect of the composition is more prominent.

In one embodiment the composition is administered both during early infancy (first 6 months) and/or 6 months-1 year and during older infancy (e.g. 1 to 4 years or 2 to 6 years). Such administration can but may not be daily but may be sufficiently regular (e.g. at least once every month or week) to induce the intended effect. A continuous administration over a long period of time (a few years), although relatively infrequent (one per week, once to 4 times per month), may enhance the observed effect by acting at the critical phase of the immune system maturation.

In regard to the use of the composition of the invention the children, babies or infants can be allergic children. Allergic children are those children, babies or infants having experienced at least one episode of allergic reaction—light, moderate or severe—to a food allergen. In one embodiment of the invention the children, babies or infants have declared severe allergies to food allergens and/or have experienced more than one moderate or severe episode of food allergy.

The food allergens encompassed by the present invention can include all types of allergens naturally occurring or usually occurring in food, especially food for young humans (e.g. infants, babies, children).

Experimental Results:

In vitro studies with human and rodent cells have suggested that anti-oxidants may modulate mast-cell function. As fruits and vegetables are rich in anti-oxidants we addressed whether symptoms of food allergy could be influenced with a fruit extract. Specifically, we tested the effect of consuming apple extract Pomactiv HFV in a mouse food allergy model (OVA Food Allergy Mouse Model, illustrated in FIG. 1).

Figure 2:
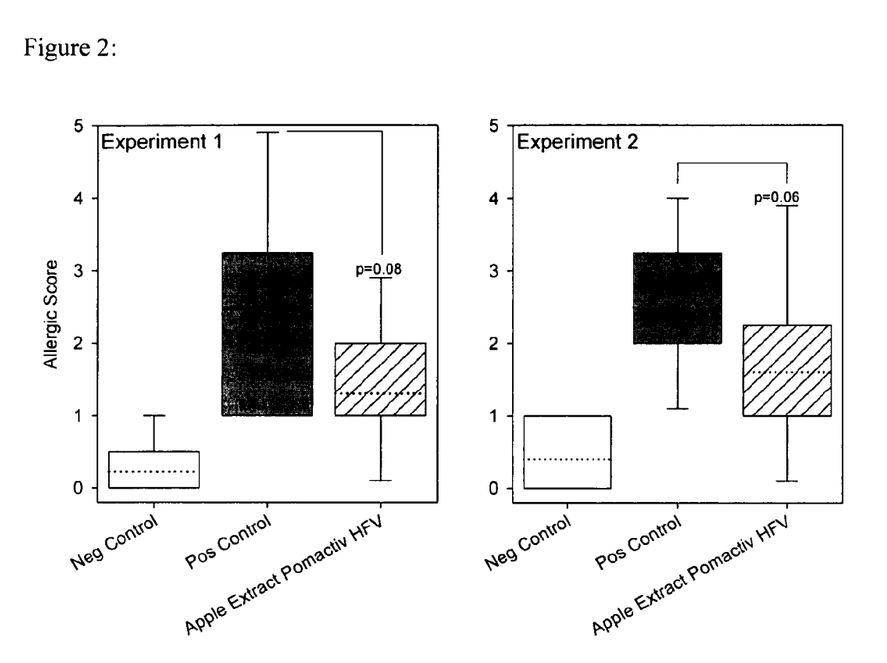
FIG. 2: Reduced symptoms of food allergy in mice receiving 1% of apple extract during the last week before allergen challenge. Results of 2 independent experiments.

After challenge mice treated with apple extract developed less severe clinical symptoms than sensitized, untreated animals (Positive Control). These results are illustrated by the experimental results shown in FIGS. 2 and 3:

FIG. 2 shows the results of 2 independent exploratory experiments conducted with 10 animals/group. The measured output (allergic score) shows a positive trend in the reduction of the allergy score in mice having received Apple extract in comparison to the positive control. ($p=0.08$, 0.06 respectively).

Figure 3:
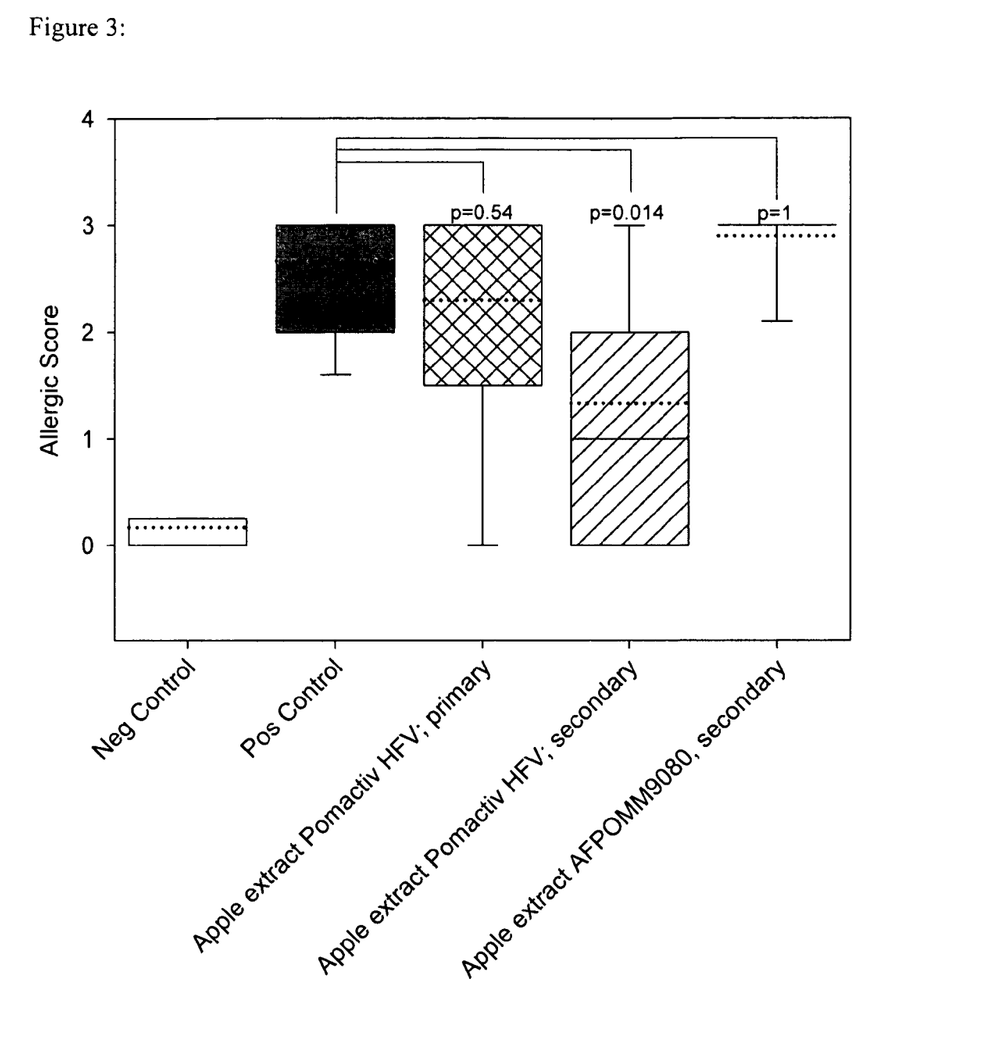
FIG. 3: Reduced symptoms of food allergy in mice receiving 1% of apple extract (Pomactiv HFV or Diana Naturals AFPOMM9080) either during sensitization period (primary) or during the last week before allergen challenge (secondary).

FIG. 3 shows the results of a statistically powered experiment ($n=15$/group) in the same model. The effect of reduction of the allergy score in the group receiving Apple extract during the last week before challenge (secondary prevention) was confirmed and was statistically significant (FIG. 3; $p=0.014$, group "apple extract Pomactiv HFV, secondary). A group treated with the same apple extract during the sensitization phase (group "apple extract Pomactiv HFV, primary) did not show reduced symptoms after challenge. Likewise, a group treated with a different apple extract did not have reduced symptoms after challenge (FIG. 3, group Diana Naturals AFPOMM9080).

Figure 4:
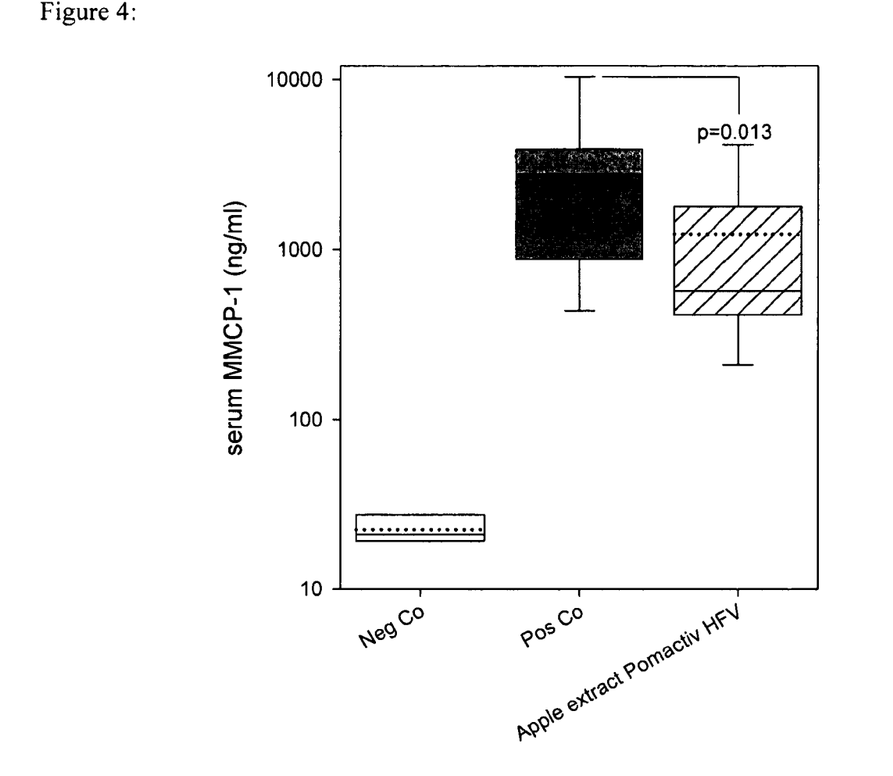
FIG. 4: Median levels of Mouse Mast-Cell Protease 1 (MMCP-1) in sera 4 hours after challenge.

In addition to the clinical score, mouse mast-cell protease 1 (MMCP-1) serum levels were determined as a measure of intestinal mast-cell activation by allergen challenge. Consumption of apple extract Pomactiv HFV significantly reduced MMCP-1 serum levels compared to non-treated control animals (FIG. 4).

Figure 5:
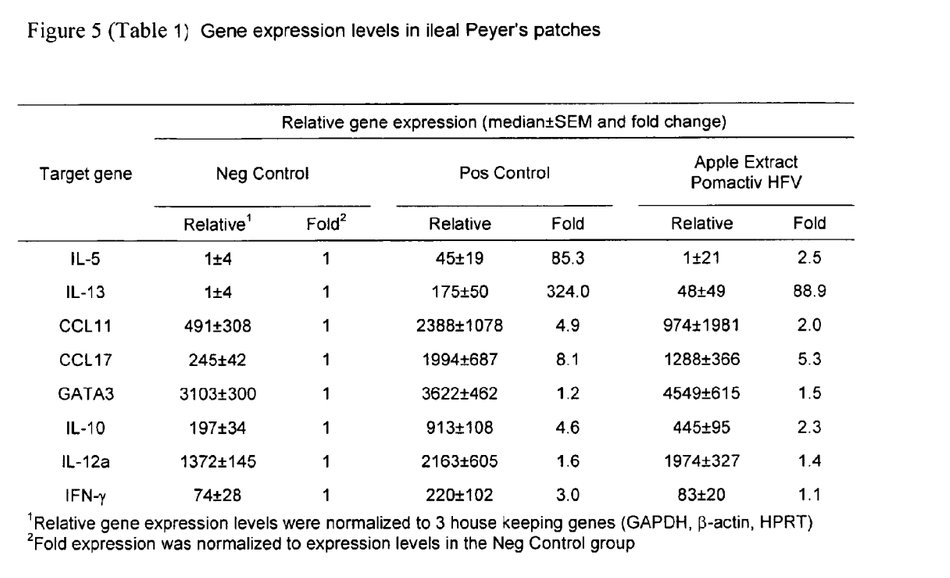
FIG. 5/Table 1: Gene expression levels in ileal Peyer's patches
Figure 6:
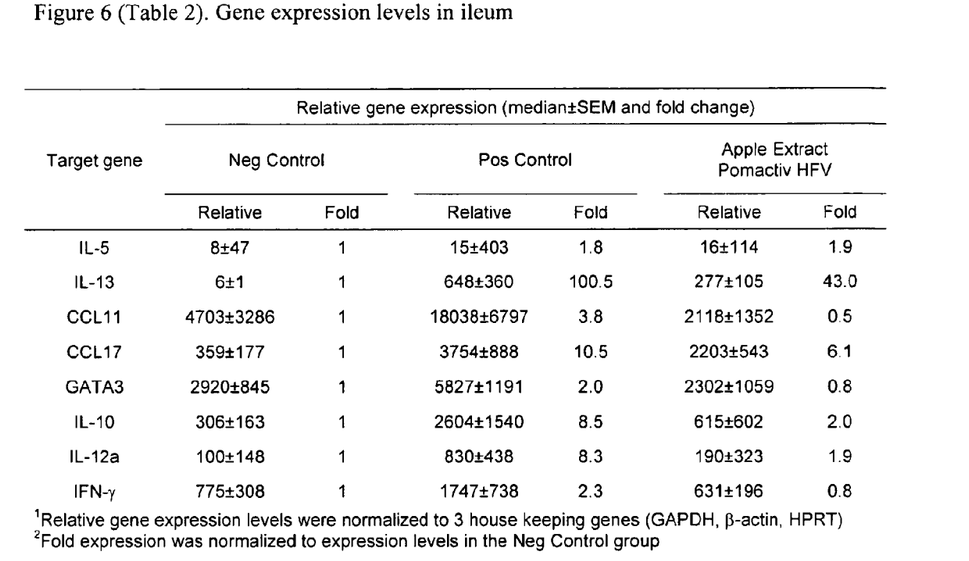
FIG. 6/Table 2. Gene expression levels in ileum

Expression levels in the intestine of various genes associated with allergy were determined by quantitative real-time polymerase chain-reaction (qRT-PCR—see method below). The measurements of gene expression were performed on tissues from 2 different sites (Ileal Peyer's Patch and ileum for the positive control group, the negative control group and the group receiving Apple extract (Pomactiv HFV) during the last week before challenge (secondary prevention). FIG. 5 (Table 1) and FIG. 6 (Table 2) illustrate the results obtained: The group receiving Apple extract Pomactiv HFV exhibited a reduced expression of various genes, including cytokines interleukin (IL)-5, IL-13, IL-10, interferon (IFN)-γ and chemokine CCL11 (eotaxin) in ileal Peyer's Patches and cytokines IL-13, IL-10, IL-12, IFN-γ, chemokine CCL11 (eotaxin) and transcription factor GATA-3 in ileum. The genes for which reduced expression has been evidenced are generally recognized markers for a T helper 2 phenotype (IL-5, IL-13, CCL11, GATA-3) which is known to drive development of allergies. Hence the experiments demonstrate the down-modulation of immune responses by reduction of expression of relevant genes when the sensitized animals received Apple extract (secondary prevention). This is believed to be contributing to the anti-allergic effect of the tested Apple extract in the reduction of allergic symptoms (secondary prevention).

Conclusion:

These data show that consumption of a polyphenol enriched apple extract (Pomactiv HFV) by a sensitized animal leads to reduced allergic symptoms upon exposure to the sensitizing allergen. The reduction of symptoms went along with reduced serum levels of MMCP-1 and reduced expression of key genes related to allergy in the intestine, suggesting that a modulation of components of the immune system, such as mast-cells, contributes to the protective effect.

Figure 1:
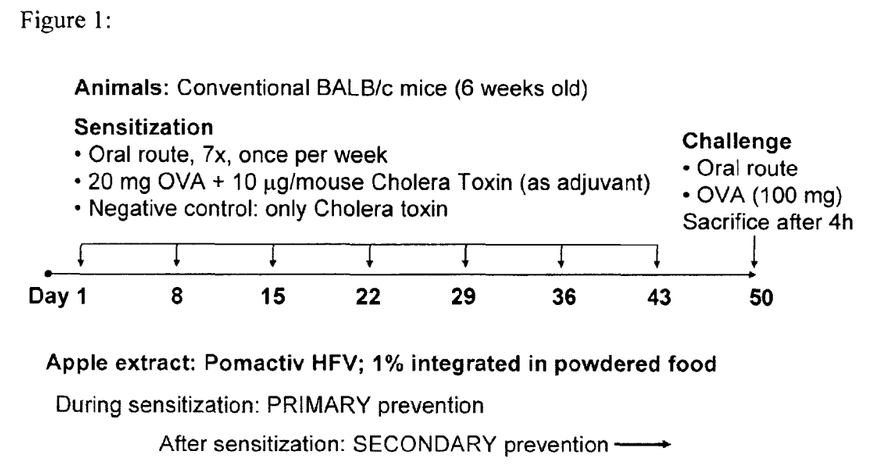
FIG. 1: Schematic description of OVA food allergy mouse model

Analytical methods:

OVA Food Allergy Mouse Model:

Six weeks old adult conventional BALB/c mice were sensitized by the oral route (with a gavage needle) at weekly intervals with 20 mg of Ovalbumin (OVA) from Fluka (Buchs, Switzerland) +10 µg/mouse of Cholera toxin (used as adjuvant) from LuBioscience (Lucerne, Switzerland) during 7 weeks. One week after the last sensitization an oral challenge with 100 mg of OVA was performed. Nutritional intervention with apple extract HFV from Val de Vire Bioactives (Val de Vire Bioactives—BP2-50890 Conde sur Vire, France, catalogue reference: "Pomactiv HFV") or AFPOMM9080 from Diana Naturals (Antrain, France) (1% w/w) incorporated into the food (Kliba 3200, Kliba Nafag Kaiseraugst, Switzerland) was done all along the experiment; as a primary prevention during sensitisation period or as a secondary prevention starting at the end of the sensitization phase (FIG. 1). Fifteen minutes after challenge mice were individually observed during 30 min. Clinical symptoms were recorded and quantified as follows (Allergic Score): 0: no symptoms, less than 4 episodes of scratching; 1: 4-10 episodes of scratching around the nose and head, no diarrhoea; 2: more than 10 episodes of scratching or bristled fur and immobility or soft stool; 3: diarrhoea or laboured respiration or cyanosis; 4: diarrhoea in combination with immobility after prodding, bristled fur, laboured respiration or cyanosis; 5: anaphylaxis. Four hours after challenge mice were sacrificed (cervical dislocation), blood and the last centimeter of ileum plus one Peyer's patch located in the same area were taken and frozen in liquid nitrogen.

Serum MMCP-1:

Murine mast cells protease 1 (MMCP-1) was quantified in mouse serum by ELISA, purchased from Moredun Scientific (Midlothian, Scotland) according to the manufacture's instructions. The MMCP-1 concentration was obtained by converting OD values in pg/ml using a polynomial standard curve.

Low Density Array analyses of Gene Expression in Intestine:

RNA Extraction and Quantification:

Total ribonucleique acids (RNA) from Ileum and Peyer's patch were extracted according to the manufacture's protocol using SV Total RNA isolation System kit purchased from Promega (Dübendorf, Switzerland).

RNA was quantified with quant-IT Ribogreen Reagent kit provided (Promega Dübendorf, Switzerland) according to the manufacture's protocol.

Reverse Transcription:

Reverse transcription was performed on 1 µg of total RNA by using the Multiscribe Reverse Transcriptase kit from Applied Biosystems (Foster City USA). Total RNA was mixed with 50 µM of random hexamers, 0.5 mM of dNTPs, 20 U of RNase inhibitor (Applied Biosystems), 62.5 U of Multiscribe reverse transcriptase, 1X RT buffer, and 5.5 mM of MgCl2 in a final volume of 50 µl. Reverse transcription was run on a T3 thermocycler (Biometra, Göttingen, Germany) with the following cycle program: 10 min at 25° C., 30 min at 48° C., 5 min at 95° C. to finish at 4° C.

LDA:

Low Density Arrays were designed online on the Applied Biosytems website (http://www3.appliedbiosystems.com/index.htm). The load, the run and the analysis were performed according to the manufacturer's protocol on a quantitative ABI-Prism 7900HT.

The quantification was normalized with the mean of 3 houses keeping genes: β-actin, GAPDH and HPRT. Based on the Cycle threshold (Ct) values obtained, a relative and normalized mRNA expression was determined for each gene using the ΔCt. The Ct value for each gene was corrected by the Ct mean of the three house keeping genes. The results were calculated as a relative expression using the formula $-2-\Delta Ct \times K$ were K is a $10^6$ factor. Fold increase results expression was normalized to expression levels in the Negative group.

The invention claimed is:

1. A method for reducing the symptoms of allergies originating from food in patients having allergies triggered by food allergens comprising the step of administering a nutritional composition comprising vitamins, minerals, a source of protein comprising essential amino acids, a source of lipids comprising essential fatty acids, and a source of carbohydrates and comprising an apple extract comprising at least 40% polyphenols, and flavonols are present in the apple extract in an amount of 20-35% of the polyphenols, to the patient.

2. The method of claim 1 wherein the composition provides secondary prevention against allergic reactions triggered by the food allergens.

3. The method of claim 1 wherein the composition has no effect on the sensitization of the patients to the allergens.

4. The method of claim 1 wherein the composition comprises between 0.1% w/w to 1% w/w of the apple extract.

5. The method of claim 1 wherein the composition comprises quercetin.

6. The method of claim 1 wherein the composition comprises hydrolyzed proteins.

7. The method of claim 1 wherein the composition reduces the sensitization to other allergens later in life.

8. The method of claim 1 wherein the symptoms are selected from the group consisting of diarrhea, skin irritation, respiratory and combinations thereof.

9. The method of claim 1 wherein the composition comprises cereal proteins.

10. The method of claim 1 wherein the patient is a human selected from the group consisting of an infant up to 6 months old, an infant after the first 6 months of life, and a child between 1 and 6 years of age.

11. The method of claim 1 wherein the composition is an infant cereal composition and is administered to a human infant 1 to 4 years old.

12. The method of claim 1 wherein the composition is administered to a human infant during the weaning period and/or up to 12 months thereafter.

13. The method of claim 1 wherein the patients are human infants or young children below the age of six.

14. The method of claim 1 where the symptoms are accompanied by a release of biochemical mediators.

15. The method of claim 1 wherein the composition has no effect on the sensitization of the patients to the allergens, and the composition comprises between 0.1% w/w to 1% w/w of the apple extract.

* * * * *